(12) United States Patent
Stirbl et al.

(10) Patent No.: US 7,133,725 B2
(45) Date of Patent: Nov. 7, 2006

(54) METHOD AND RELATED COMPOSITION EMPLOYING NANOSTRUCTURES

(75) Inventors: Robert C. Stirbl, Pasadena, CA (US);
Malcolm L. Snead, Valencia, CA (US);
Jimmy Xu, Providence, RI (US); Ellen S. Vitetta, Dallas, TX (US); Peter J. Wilk, New York, NY (US)

(73) Assignee: Wilk Patent Development Corporation, New York, NY (US)

( * ) Notice: Subject to any disclaimer, the term of this patent is extended or adjusted under 35 U.S.C. 154(b) by 650 days.

(21) Appl. No.: 10/322,892

(22) Filed: Dec. 18, 2002

(65) Prior Publication Data

US 2003/0171257 A1    Sep. 11, 2003

Related U.S. Application Data

(60) Provisional application No. 60/342,894, filed on Dec. 19, 2001.

(51) Int. Cl.
*A61N 5/00* (2006.01)

(52) U.S. Cl. .................. 607/100; 607/96; 607/103; 607/1

(58) Field of Classification Search .............. 607/1, 607/2, 4, 9, 96; 600/300; 128/897–899
See application file for complete search history.

(56) References Cited

U.S. PATENT DOCUMENTS

| | | | |
|---|---|---|---|
| 6,329,503 B1 | 12/2001 | Afar et al. ................. 530/350 |
| 6,330,472 B1 | 12/2001 | Sukumar ..................... 604/21 |
| 6,613,875 B1* | 9/2003 | Ghadiri ...................... 530/321 |
| 2001/0051766 A1* | 12/2001 | Gazdzinski ................. 600/309 |
| 2002/0061591 A1* | 5/2002 | Choong et al. ............. 435/450 |
| 2002/0122810 A1* | 9/2002 | Cubicciotti ................. 424/400 |

* cited by examiner

*Primary Examiner*—Carl Layno
(74) *Attorney, Agent, or Firm*—R. Neil Sudol; Henry D. Coleman; William J. Sapone

(57) ABSTRACT

A composition of microscopic devices utilizable in a medical diagnostic or therapeutic procedure. Each microscopic device includes a nanostructure provided with a ligand for effectively coupling the nanostructure to a predetermined chemical or molecular site. A medical method in part comprises inserting the medical devices into a patient, attaching the nanostructures via the respective ligands to instances of a predetermined type of target structure inside the patient, and thereafter activating the nanostructures to perform a preselected medical diagnostic or therapeutic function.

26 Claims, 3 Drawing Sheets

METHOD AND RELATED COMPOSITION EMPLOYING NANOSTRUCTURES

CROSS-REFERENCE TO RELATED APPLICATION

This application claims the benefit of U.S. provisional patent application No. 60/342,894 filed Dec. 19, 2001.

BACKGROUND OF THE INVENTION

Generally, this invention relates to a composition containing nanostructures such as nanotubes. This invention may be used in a medical method, therapeutically and/or diagnostically.

Despite the ever accelerating advances in medical technology, there are many disease states which present medical techniques are unable to adequately treat. For example, there is no effective treatment of nerve tissue damage. Extant therapies for other illnesses are only partially effective in most people. Such illnesses or afflictions include gout, excess weight, bone injuries, aging, and cancer. In addition, while other disease states or systemic malfunctions are treatable by current methods, the treatments frequently have disadvantages or undesirable side effects. For example, in the treatment of cardiac arrhythmias, pacemakers are implanted in the patients, thus requiring open surgery with the attendant risks, costs, and traumas. Drugs used in the treatment of AIDS have serious side effects such as toxicity and rapid rise of resistant viral strains.

SUMMARY OF THE INVENTION

The present invention is directed in part to a generally applicable medical methodology which may be used in the treatment of many kinds of injuries and diseases, whether of an infectious nature, a genetic nature, systemic, localized. The present invention is also useful in the acquisition of information for the performance of medical diagnoses.

The present invention is more generally directed to a composition of matter including nanostuctures. The nanostructures are functionalized in the sense of being provided with coupling ligands for enabling the targeting of the nanostructures to predefined sites.

In brief, the present invention is specifically directed to the insertion or implantation or targeting into patients of microscopic or submicroscopic devices at predetermined target sites. The microscopic devices are manufactured items each at least partially inorganic in composition. The insertion or implantation may be effectuated through open surgery, minimally invasive techniques, injection into the vasculature, or in some cases, through ingestion by the patient.

It is contemplated that the medical devices are in an inactive state prior to insertion in the patient and during transport through the patient to a target site in the patient. This transport may be accomplished through the natural functions of the body, for instance, through the individual patient's vascular system, endocrine system, digestive tract, and/or lymphatic system, etc. Alternatively or additionally, there may be a more direct conveyance of the medical devices to their respective target sites. For instance, the devices may be deployed in the patient through a catheterization process (e.g., vascular), an endoscopic or laparoscopic procedure, hypodermic injection, etc.

The present invention contemplates that the microscopic or submicroscopic medical devices become effectively attached to cellular or molecular target structures at the respective target sites. These target structures may take the form of protein segments embedded, for instance, in cellular or viral membranes. The targets may be viral antigens expressed in infected cells of a host organism. In any case, the proteins are markers for the particular kind of target cell, while effective attachment is preferably effectuated via ligands in the form of antibodies or cognate proteins (polypeptides). These ligands are provided as connector elements on the microscopic devices during the manufacturing process.

Pursuant to the present invention, the microscopic medical devices take the form of nanostructures, that is, fabricated elements having a nanometer to micrometer size. A medical device such as a battery may comprise a single nanostructure. Alternatively, a microscopic medical device may comprise several nanostructures which are separately inserted into the patient and which self-assemble to form a more complex device inside the patient, for instance, at a target site. Self-assembly is effectuated by providing members of a connecting pair of nanostructures with respective cooperating or interlocking ligands. The nanostructures thus seek each other out and self-attach in the same manner as one or more nanostructures attach to a target molecule at a target cellular site.

Accordingly, a medical method in accordance with the present invention utilizes an implantable microscopic medical device including a nanostructure provided with a ligand. The method in part comprises inserting the medical device into a patient, effectively attaching the targeting nanostructure via the ligand to an instance of a predetermined type of target structure inside the patient, and thereafter utilizing the nanostructure to perform a preselected medical diagnostic or therapeutic function.

Typically, the target structure is a cellular structure such as a membrane protein or an instance of messenger RNA. However, the target structure may be an extracellular substance such as urea deposits or intravascular plaque. In some instances, the mere attachment of the nanostructure to the target structure will be sufficient to destroy the target structure. Where the target structure (e.g., protein) is embedded in a larger structure (e.g., cell membrane), that larger structure may be ruptured or destroyed as well. In other instances, the utilizing of the attached nanostructure entails an activation of the nanostructure. The activation may be implemented by a change in shape or dimension of the nanostructure and the introduction of energy into the reshaped nanostructure by induction. Alternatively or additionally, the activating of the nanostructure may be implemented by an attachment of the nanostructure to other nanostructures. For instance, the change in the shape or dimension of the nanostructure may be accomplished in whole or in part by a connecting of the nanostructure to other nanostructures. Or the attachment may result in an electrical device which may be operated to perform a predetermined function.

Where the target structure is messenger RNA, the nanostructure is utilized to destroy the mRNA. This destruction may be effectuated by mere attachment of the nanostructure via the ligand or may be effectuated in part by the heating of the nanostructure. The destruction of mRNA is beneficial, for example, where the mRNA is implicated in the replication process of a virus.

The nanostructure is frequently inserted into the patient in a deactivated or non-active state. After attachment to the target structure, the nanostructure is activated as part of the utilization procedure. The nanostructure may be provided with at least one additional ligand. In that event, the activating of the nanostructure includes coupling the nanostructure via the additional ligand to another nanostructure deployed in the patient. The two coupled nanostructures assemble in the patient to form, for instance, an electrical device or circuit. Then, the activating of the nanostructure further includes operating the electrical device. In one embodiment, the electrical device includes a nanobattery, or a series or parallel coupling of nanobatteries, and the activating of the nanostructure includes using a body fluid to enable ion migration under a potential generated by the battery. The nanostructure may be passivated, except at its ends, to insulate the structure from electrolytic action of the body fluids. In addition, end cap structures may be provided to temporarily insulate the ends of the nanostructure from the body fluids. The end caps may be made of a biocompatible material such as a polymer which dissolves in body fluids. In a more specific realization of the invention, the electrical device includes a timing circuit, with the activating of the nanostructure including generating an electrical event periodically under the action of the timing circuit. This electrical device may function as a pacemaker. In that case, the devices are anchored to a predetermined site, e.g., a structural site, in cardiac tissue.

A nanobattery circuit assembled in situ in accordance with the present invention may include a timing element in the form of an organic or inorganic structure, such as a single molecule, energized in body fluid to produce pulses of electricity, changes of resistance to modulate a battery circuit. A molecular structure is configured to have its conductivity in a particular direction modulated by a flow of ions around the circuit in a fixed or variable way.

In another particular procedure pursuant to the present invention, a nanostructure may be anchored proximately to an injury site in a nerve, together with millions or billions of similar nanostructures) for purposes of facilitating an effective repair of injured nerve tissue, to restore nerve conduction. The nanostructures serve in the generation and/or conduction of electrical current in the injured nerve tissue. This electrical current may be generated via a battery assembled in situ at the site of the nerve cell injury. Alternatively, the electrical current may be generated inductively. The inducing of the current includes generating, outside of the patient, an energy field and subjecting the nanostructures inside the patient to the energy field.

Where the predetermined type of cellular structure includes a protein or protein segment, the ligand on an implanted nanostructure may include a polypeptide or antibody selected to couple with the protein or protein segment. This protein may a marker for a particular kind of cell, for instance, a cancer cell, a fat cell, or a viral infected cell, and disposed in the wall or membrane of the cell. In that event, the nanostructure is activated to destroy the cell. In one form of activation pursuant to the present invention, the nanostructure attached to the protein is heated, either inductively or via a nanobattery assembled through ligand interaction at the target site. The heating of the nanostructure results in a disruption or rupture of the cell membrane and concomitantly a fragmentation or lysis of the targeted cell.

Pursuant to the present invention, destruction of an undesirable cell may be effectuated by inserting a nanostructure into the cell and thereafter heating the nanostructure. The insertion may be accomplished by attaching the nanostructure to a target transport mechanism on the surface of the cell, by coating the nanostructure with a protein sheath which is subject to absorption by a cell, or by attaching the nanostructure to a virus which is transported through the cell membrane. The attachment of the nanostructure treatment device to the virus carrier may take place in vivo or in vitro.

A ligand in the form, for instance, of a nucleotide sequence, polypeptide or antibody may be attached to a nanostructure via a polymer, pursuant to known techniques. Alternatively, the attachment may occur via an avidin-biotin or streptavidin-biotin link.

In accordance with another feature of the present invention, the activating of a nanostructure deployed in a patient is implemented in part by changing a physical dimension of the nanostructure. This change in physical dimension may occur automatically by virtue of the attachment of the nanostructure via a ligand to an instance of the predetermined type of cellular structure. The purpose of having the nanostructure change in dimensions is to change a resonance characteristic of the nanostructure. Prior to the change in dimension, the nanostructure is unreceptive or impervious to an energy field of a particular frequency or wavelength. After the change in dimension or size, the nanostructure absorbs energy from the field, whereby current flows and heat is resistively generated.

Where an implanted nanostructure is heated inductively, the nanostructure may be completely passivated, i.e., completely enclosed in a protective or insulating sheath. Alternatively, a nanostructure such as a nanotube may be heated by connecting the nanostructure to a "nanobattery" in a "nanocircuit." That circuit may be substantially isolated from body fluids. Alternatively, the circuit may include a segment or path extending through body fluids of the patient.

Where an implanted nanostructure functions as a battery, the nanostructure has opposing ends provided with elements of different valences or electron affinities. The activating of the nanostructure includes using a body fluid to enable ion migration under a potential generated between the minerals. Alternatively, the nanostructure may be provided with mutually spaced magnetic, paramagnetic, or diamagnetic elements, currents being generated by the motion of charged magnetic particles.

As mentioned above, a nanostructure may be inserted into a patient by injection through a lumen of a medical instrument such as a hypodermic syringe, catheter, or endoscopic instrument having an end portion disposed in the patient.

A related medical composition comprises, in accordance with the present invention, a biocompatible or pharmaceutically acceptable fluid carrier or matrix, and at least one microscopic medical device including a nanostructure provided with a ligand, the medical device being disposed in the carrier or matrix. The ligand is attachable to a predetermined type of cellular structure inside a patient, while the nanostructure is activatable, after attachment of the nanostructure to an instance of the cellular structure via the ligand, to perform a preselected medical diagnostic or therapeutic function.

The nanostructure may be provided with at least one additional ligand couplable to another nanostructure after an insertion of the matrix with the medical device into the patent. The two nanostructures may be configured to form an electrical circuit upon coupling of the nanostructures via the additional ligand or functionalized complex.

The nanostructure may include an electrical circuit element such as a battery cell, a monostable multivibrator, a timer, resistive, capacitive, and/or inductive elements, and a chemical sensor or receptor.

A medical composition in accordance with the present invention comprises an effective number or concentration of microscopic medical devices each including a nanostructure provided with a ligand effectively attachable to a predetermined type of target structure inside a patient. The nanostructure is utilizable, after an effective attachment of the nanostructure to an instance of the target structure via the ligand, to perform a preselected medical diagnostic or therapeutic function.

As discussed above, each nanostructure may be provided with at least one additional ligand couplable to another nanostructure after an insertion of the matrix with the medical device into the patent, while the ligand may be taken from the group consisting of an antibody and a peptide sequence, the predetermined type of target structure being taken from the group consisting of a protein and a polypeptide.

Pursuant to the present invention, each nanostructure may be provided with a masking agent such as albumin for blocking coupling sites on such nanostructure that are free of the ligand.

A method and a related composition in accordance with the present invention provide a new era in medical treatment and diagnosis. The war against viral and bacterial infections, as well as against cancer, can be carried forward now on a cellular level using microscopic and submicroscopic devices.

The present invention more generally contemplates a composition comprising microscopic devices each including at least one nanostructure provided with at least one ligand for effectively attaching the nanostructure to a predetermined type of target structure. This composition may be used in medical or nonmedical applications. The nanostructures of the microscopic devices have covalent bonding sites which in one embodiment of the invention are saturated with ligands. Alternatively or additionally, the nanostructures of the microscopic devices are provided with at least one masking agent for blocking coupling sites on the nanostructures free of ligands. As discussed above, the nanostructures may be each provided with at least one ligand couplable to another nanostructure.

DEFINITIONS

Figure 1:
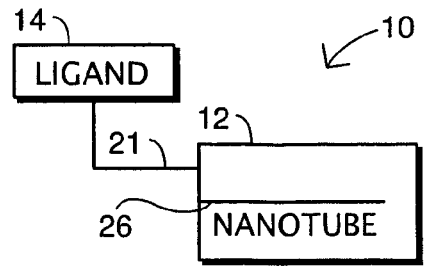
FIG. 1 is a block diagram of a nanostructure and connector ligand, in accordance with the present invention, showing the nanostructure in an inactive transport configuration.

The term "nanostructure" is used herein to denote a partially inorganic component of a nanometer scale or size. More particularly, a nanostructure pursuant to the present invention has a diameter or edge size between about 1 nanometer and about 1 micron. A nanostructure in accordance with the invention may simply be a metal particle, either naturally occurring and harvested for purposes of medical treatment and/or diagnosis or fabricated. A nanostructure as described herein may be a simple carbon nanotube, a simple circuit element such as a diode, capacitor, inductor, transistor, or a more complex circuit element such as a monostable multivibrator, oscillator, time base, or molecule detector. In the latter case, the nanostructure may incorporate an organic structure such as a molecule serving as a receptor for monitoring the presence of a preselected molecule such as hormone or enzyme. Where the nanostructure is a nanotube, it may function as a filament for connecting more complex circuit elements. Alternatively, a nanotube may function as a heating element or battery cell. In the former case, the heating may be accomplished inductively, with the nanotube being energized by an external energy field. In the latter case, the nanotube may be provided at opposite ends with chemical elements such as zinc and copper (or carbon) having different electron affinities and perhaps combined with cathode or anode improving chemical agents.

The word "microscopic" is used herein to denote objects having a size in a range between about 1 nanometer and about 1 micron. Thus, the word "microscopic" as used herein generally includes objects (e.g., nanostructures) that are submicroscopic (as far as optical microscopes are concerned). In some cases, an electrical device constructed in a patient from self-assembling nanostructures may have a size as large as microns or hundreds of microns.

The prefix "nano-" is used herein in combination with different electrical elements or devices to indicate that such elements or devices are of a microscopic or submicroscopic size.

The word "bent" or "folded" is used herein with reference to a nanostructure to indicate that the nanostructure has more than one configuration or shape, with the bent or folded configuration being modifiable, for instance, inside a patient to another configuration. The bent or folded configuration is advantageously, but not exclusively, used as an inactive transport conformation of the nanostructure, the other configuration being an active or activatable conformation. Thus, the nanostructure may be preserved during the delivery process and then shifted into a useful form for performing a predetermined function. Generally, the folded or bent configuration of a nanostructure is smaller than a relaxed or lower-energy conformation of the nanostructure. Thus, a nanostructure may be injected into a patient in a transport or pre-activation conformation in which the nanostructure is dormant. In this conformation, the nanostructure is not receptive of a preselected wavelength of energizing radiation (magnetic, electromagnetic, or particulate or nuclear). In one embodiment, upon coupling of the nanostructure to a target site inside a patient, the binding energy exerted on the nanostructure falls below a requisite minimum, thus enabling a natural unfolding or expansion of the nanostructure under internal spring forces. In the expanded or relaxed conformation, the nanostructure is receptive of the preselected wavelength of energizing radiation, thus enabling, for instance, a heating of the nanostructure through an inductive process.

The term "target structure" as used herein designates refers to a microscopic or submicroscopic structure, for example, in a patient, to which it is desired to attach a nanostructure-implemented medical treatment or diagnostic device. The term "target structure" may designate an entire cell, but more particularly denotes a cellular structure, i.e., an organic molecule such as a protein, nucleotide chain, carbohydrate, or lipid, which is located inside a biological cell, on a cell membrane, in intercellular spaces, or in a body fluid such as blood or lymph. The term "cellular structure" concomitantly also denotes a larger structure such as a cell or virus.

The phrase "instance of a predetermined type of target structure" as used herein designates, in medical applications, a specific cell, virus, molecule, cellular or molecular fragment, a noncellular structure such as arterial plaque or urea deposits, etc. In other applications, the phrase "instance of a predetermined type of target structure" is used herein to designate any microscopic structure such as a molecular or a crystalline lattice to which nanostructures may be effectively coupled or attached.

The word "activating" means generating a state of a nanostructure in which the nanostructure is operative to accomplish a predetermined function, for instance, for purposes of enabling a diagnosis or treatment of a patient on a cellular or molecular level. Thus, a nanostructure may be activated by expansion from a folded, transport configuration to an opened active configuration capable of absorbing energy packets from a field generated, for example, in a patient, by an external source. Another nanostructure such as a circuit element might become activated by coupling of the circuit element in a functional circuit. Yet another nanostructure such as a nanotube or a metal particle might become activated simply by coupling of the nanostructure to the respective target structure.

The word "passivated" as used herein refers to the provision of one or more protective layers about a nanostructure to insulate the nanostructure from interference in an environment in which the nanostructure is to be used, e.g., by a patient's natural body chemistry. For instance, a passivated nanostructure pursuant to the present invention may be formed with a layer of silicon or other biocompatible and effectively inert material for preventing electrical grounding or short-circuiting of the nanostructure by electrolytes in the body and/or for deflecting an attack from the body's immune system and/or for inhibiting the deposition or precipitation of ions such as calcium ions and phosphates. Thus, one or more passivation layers may be for electrical insulation purposes, biochemical neutralization purposes, etc. A passivation layer may be permanent, that is, have an effective life span equal to the life span of the respective nanostructure. Alternatively, a passivation layer may be designed to disintegrate after a predetermined period of time in body fluids or upon occurrence of a predetermined event, such as attachment of the nanostructure to a respective target structure. Carbon nanostructures, including those with nonspecifically bound ligands, may be passivated by a coating of a natural body protein such as albumin.

The word "implantable" is used herein to describe a nanostructure that is insertable into the human body. An implantable nanostructure is substantially biocompatible. Implantation of a nanostructure in accordance with the present invention may be effectuated by any of several known techniques, including injection by syringe, endoscope biopsy channel, laparoscopic instrument, or catheter. Implantation of a nanostructure in accordance with the present invention may be effectuated by a minimally invasive technique or by open surgery. The method of implantation will vary in accordance with the purpose of the nanostructure, its target structure, the condition of the patient, the preferences of the physician, etc.

A "ligand" as that term is used herein refers to a chemical structure capable of and selected because of its bonding affinity for a determined type of cellular or molecular or inorganic structure. A ligand pursuant to the present invention may bond to a cellular or molecular structure already present in the tissues of the patient or may bond to a molecular structure—another ligand—inserted into the patient. Ligands can include antibodies, antibody-coated liposomes, polynucleotides, polypeptides, soluble receptors, viral plasmids, polymers, proteins, etc. Ligands are selected in accordance with the desired target structure. Thus, antibodies are used where the target structure is an antigen or protein segment, for instance, a cell-surface or a transmembrane protein expressed by virtue of a cellular dysfunction such as a viral infection or a cancer. Antibody-coated liposomes may be used to target the same antigens or polypeptides, the liposomes containing a payload of nanostructures functionalized with ligands such as polynucleotides designed for latching onto complementary DNA strands such as viral DNA strands inside infected host cells. Ligands may be coupled to a nanostructure via covalent bonding or nonspecific bonding. A nanostrcuture may carry multiple ligands of different types.

The phrase "effective attaching" refers herein to a coupling of a nanostructure, via a ligand on the nanostructure, to a target receptor, antigen, molecule, or other chemical structure where the coupling is of sufficient integrity to permit the use of the nanostructure in a contemplated diagnostic or therapeutic procedure. The coupling may be weak but is strong enough to maintain the nanostructure in proximity to the target structure until the nanostructure is activated.

An "effective number of microscopic medical devices" refers herein to a concentration or number of nanostructure elements sufficient, when injected into a patient, to achieve an intended diagnostic or therapeutic result. If the purpose is to destroy target cells or microscopic entities of a certain type, such as cancer cells or AIDS virus particles, an effective number of microscopic medical devices is sufficient to place at least one nanostructure in proximity to each of the target cells of microscopic entities in the patient.

As used herein, the term "polynucleotide" means a polymeric form of nucleotides of at least 10 bases or base pairs in length, either ribonucleotides or deoxynucleotides or a modified form of either type of nucleotide, and is meant to include single and double stranded forms of DNA.

As used herein, the term "polypeptide" means a polymer of at least 10 amino acids.

DETAILED DESCRIPTION OF THE PREFERRED EMBODIMENTS

Figure 3:
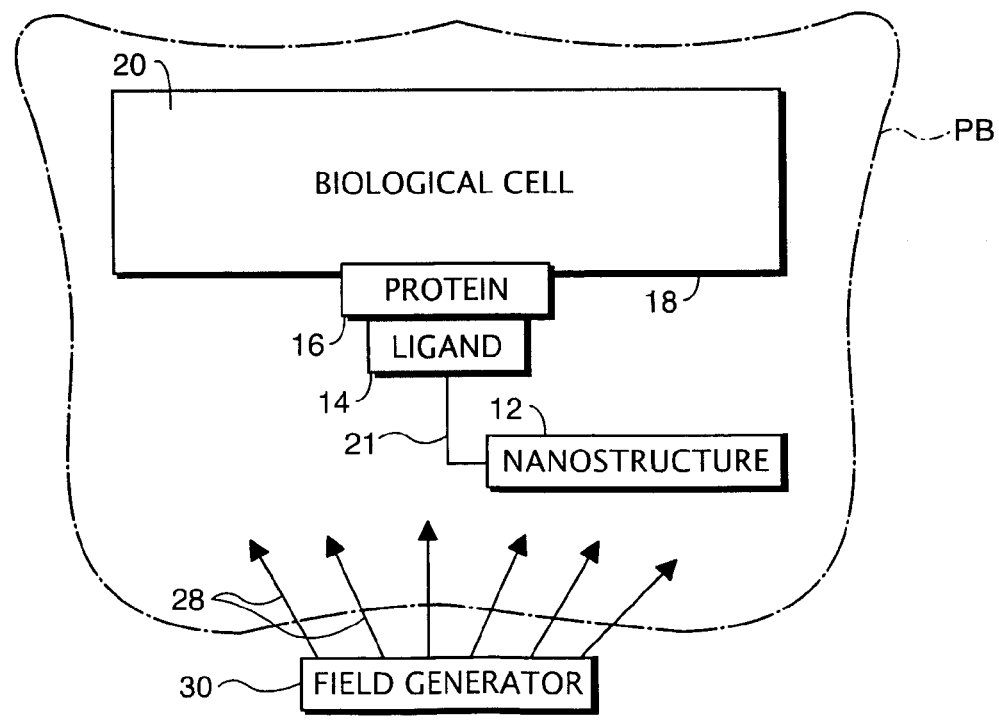
FIG. 3 is a block diagram showing an activated configuration of the nanostructure of FIGS. 1 and 2 attached via the ligand to a target protein of a target cell and further showing a field generator for inductively heating the nanostructure, in a method pursuant to the present invention.

FIG. 1 shows a transport or delivery configuration of a submicroscopic medical device 10 comprising a nanostructure 12, specifically a nanotube of a given length, provided with a ligand 14. The ligand 14 is designed and constructed to attach to a predetermined kind of target molecule in the body of a patient PB (FIG. 3). Ligand 14 is exemplarily an antibody which is selected to latch onto an amino acid sequence in a target protein 16 (FIG. 3). As shown in FIG. 3, the target protein 16 may be located in a membrane 18 of a biological cell 20 such as a cancer cell, a viral organism, or other undesirable protein-containing biological component. Alternatively, the target protein 16 may be located inside a target cell, as described in detail hereinafter. Inside a cell, a target protein may be a DNA binding protein. Outside a cell, a target protein may be a prion, such as those implicated in so-called mad-cow disease.

Ligand 14 may be attached to the respective nanostructure, specifically nanotube 12, via any suitable method. For instance, pursuant to methods well known in the art, a polymer link or magnetic particle 21 may serve as a binding component. Alternatively, avidin and biotin may be used to link ligand 14 to nanotube 12. During manufacture, streptavidin is connected to a carboxyl terminus on nanotube 12 via an amine by a dehydration reaction. (See "Covalently Functionalized Nanotubes as Nanometre-sized Probes in Chemistry and Biology," Stanislaus S. Wong et al., Nature, Vol. 394, 2 Jul. 1998, pp. 52–55.) It is then a straightforward matter to attach biotin to ligand 14 and to then link the biotinylated ligand 14 to the nanotube 12 via the streptavidin.

Figure 2:
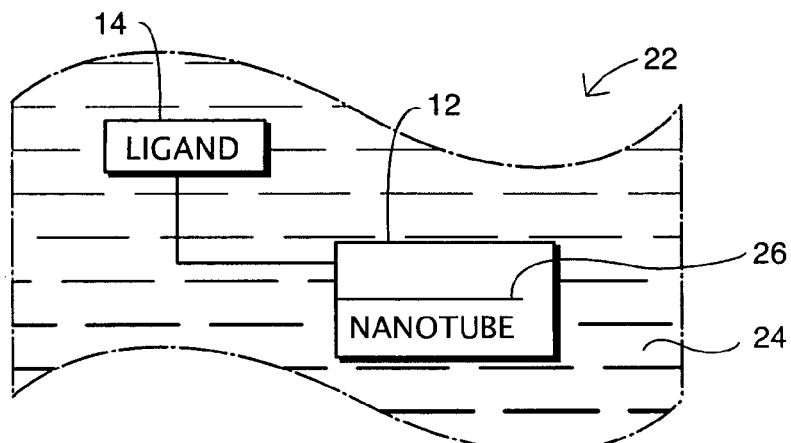
FIG. 2 is partially a block diagram showing the nanostructure and connector ligand of FIG. 1 in a biocompatible fluid matrix for the delivery of the nanostructure into a patient.

Medical device 10 of FIG. 1 is typically delivered into a patient PB as part of a medical treatment and/or diagnostic composition 22 illustrated schematically in FIG. 2. The medical composition includes a biocompatible fluid carrier matrix 24 and a multitude of microscopic medical devices 10. Carrier matrix 24 may be a saline solution, or a blood plasma in the case that the medical composition 22 is injected into the vascular system of the patient. Other kinds of biocompatible fluids suitable as a delivery vehicle are known to those skilled in the art.

Composition 22 may be delivered to the patient PB by any process suitable to the type, location and numerosity of target cells 20. Where target cells 20 are in a large tumor, delivery of composition 22 may be effectuated by simple injection into the vascular system of the patient PB, inasmuch as every large tumor has a well developed blood supply. Alternatively, composition 22 may be injected directly into the tumor, for instance, via a needle which is deployed by a physician under visual guidance provided by a camera (endoscopic, laparoscopic, etc.), a magnetic resonance imaging (MRI) apparatus, a computer-aided tomography (CAT) machine, or an ultrasonic scanner (see U.S. Pat. Nos. 6,023,632 and 6,106,463). Where the target body is a microorganism which infects a particular organ or type of tissue in the body, composition 22 may be injected directly into that organ or those tissues. Generally, intravascular injection is appropriate where a disease state is systemic, rather than localized.

In the transport or delivery configuration of nanotube 12 shown in FIGS. 1 and 2, the nanotube has a folded-over or doubled-up configuration represented schematically by a divider line 26. After the medical treatment and or diagnostic composition 22 is injected or otherwise delivered to the patient, the coupling of the ligand 14 to an instance of its target protein 16, nanotube 12 naturally springs open from the folded transport and delivery configuration of FIGS. 1 and 2 to an expanded activation configuration shown in FIG. 3. This expanded configuration is characterized by having at least one physical dimension which is larger than any physical dimension of the folded configuration, thus enabling reception by the nanotube of a predetermined wavelength or frequency of energizing energy 28 emitted into the body of the patient by an external field generator 30. Generally, field generator 30 emits energy 28 in the form of electromagnetic radiation or a magnetic field. In some cases, other forms of energy may be useful, such as mechanical vibrational energy of an ultrasonic frequency or a stream of nuclear particles. In such a case, field generator 30 takes a specific form including ultrasonic electroacoustic transducers (not shown) or a particle generator (not shown).

It is to be noted that the folded transport and delivery configuration of nanotube 12 shown in FIGS. 1 and 2 is detuned with respect to the energy 28 produced by field generator 30. Generally, in the folded transport and delivery configuration, nanotube 12 has no dimension long enough to enable absorption of the particular wavelength of the field energy 28. Thus, only those nanotubes 12 which have coupled to respective target proteins 16 via the respective ligands 14 are activated to receive energy 28. The inductive absorption of this energy by the opened or expanded nanotubes 12 heats the nanotubes at least to the point where the cell membrane 18 is disrupted or ruptured, causing destruction of the cell 20 and possibly of adjacent connected cells. This method thus serves in the treatment of cancer and infectious diseases such as AIDS, hepatitis, malaria, yellow fever, anthrax, etc. The method may also be used in the treatment of autoimmune diseases. The method is effective to destroy pathogen-infected cells of a host organism. All that is necessary is the selection of suitable target proteins 16 in the cell membranes 18 and the manufacture of antibodies each matching an amino acid sequence or peptide chain of those target proteins.

It is to be noted further that the active or energy-absorbing configuration of a nanotube 12 may be one in which the nanotube is connected to one or more other nanotubes to achieve a collective length great enough for absorbing electromagnetic energy or a predetermined wavelength. That wavelength is easily selectable to be absorbable only by the activated or assembled nano-antenna and not by any natural structure in the patient.

One particular kind of target structure for a nanostructure medical device as described herein is the messenger RNA (mRNA) of various viral species, such as the hepatitis B virus and the AIDS virus. In that case, ligand 14 of nanotube 12 is designed to attach to the target mRNA. In some cases, the very attachment is sufficient to prevent effective functioning of the particular mRNA. In other cases, effectively blocking the viral replication process requires a more active interference, such as a heating of the attached nanotube 12, thereby destroying both the nanotube and the attached mRNA.

EXAMPLE 1

Treatment of Hepatitis B Viral Infection

Below is listed a DNA sequence utilizable in whole or in part to generate a nanostructure-bearing ligand that targets the hepatitis B viral DNA, mRNA. This sequence is unique and does not target other sequences in the human genome. The targeting is specifically by p1 and p2 HBV Core Protein.

```
                                         (SEQ ID NO: 1)
ATGGACATTGACCCGTATAAAGAATTTGGAGCTTCTGTGGAGTTACTCTC

TTTTTTGCCTTCTGACTTCTTTCCTTCTATTCGAGATCTCCTCGACACCG

CCTCAGCTCTGTATCGGGAGGCCTTAGAGTCTCCGGAACATTGTTCTCCT

CACCATACAGCACTAAGGCAAGAGATTCTGTGTTGGGGTGAGTTGATGAA

TCTGGCCACCTGGGTGGGAAGTAATTTGGAAGACCCAGCATCCAGGGAAT

TAGTAGTCAGCTATGTCAATGTTAATATGGGCCTGAAAATCAGACAACTA

CTGTGGTTTCACATTTCCTGTCTTACTTTTGGAAGAGAAACTGTACTTGA

GTATTTGGTGTCTTTTGGAGTGTGGATTCGCACTCCTCTTGCTTATAGAC

CACCAAATGCCCCTATCTTATCAACACTTCCGGAAACTACTGTTGTTAGA

CGACGAGGCAGGTCCCCTAGAAGAAGAACTCCCTCGCCTCGCAGACGAAG

GTCTCAATCGCCGCGTCGCAGAAGATCTCAATCTCGGGAACCTCAATGTT

AG
```

In this example, as well as Example 2 below, the target structure is viral DNA or mRNA inside an infected cell. The ligands are designed to attach to a selected viral nucleic acid sequence. A liposomal delivery mechanism may be used. In this delivery technique, a liposome is provided with ligands specific to the cell-surface antigens or markers produced as a result of the viral infection. The liposome then adheres to the infected cell and eventually interacts with the cell membrane so as to enable release of the liposome's DNA-tagged nanostructure payload into the infected cell. The ligands are DNA strands complementary to the viral DNA and/or mRNA strands inside the infected cells and anneal to the viral DNA and/or mRNA strands. With sufficient numbers and/or sufficient energization of the nanostructures, not only the viral DNA and/or mRNA strands but the entire infected cell may be destroyed.

Examples 1 and 2 indicate that viral DNA becomes over-expressed as cell-surface proteins that are markers for the respective types of infected cells. The viral DNA may serve as a target for destroying the host cell. More generally, Examples 1 and 2 illustrate that nanostructures functionalized with ligands as described herein may be used for destroying pathogen-infected cells.

EXAMPLE 2

Treatment of HIV Infection

Below is listed a DNA sequence utilizable utilizable in whole or in part to generate a nanostructure-bearing ligand that targets the HIV viral genome using the VPR sequence (p1). This sequence appears to be specific to the viral genome and does not match any sequences in the human genome.

```
                                              (SEQ ID NO: 2)
ATGGAACAAGCCCCAGAAGACCAGGGGCCACAGAGGGAGCCATACAATGA

ATGGACACTAGAGCTTTTAGAGGAGCTTAAGAATGAAGCTGTTAGACATT

TTCCTAGGCCATGGCTCCACAGCTTAGGACAACATATCTATAACACCTAT

GGGGATACTTGGGAGGGAGTTGAAGCTATAATAAGGATATTGCAACAACT

ACTGTTTATCCATTTCAGAATTGGGTGCCATCATAGCAGAATAGGCATTA

TTCGACAGAAGAGTAAGAAATGGAGCTAGTAGATCCTAA
```

Other sequences may be selected simply by searching a listing from the appropriate Web site (e.g., of the NIH). A selected sequence could be compared by computer with the human genome to eliminate the possibility of unwanted binding to human mRNA, proteins or DNA. With respect to so-called cancer genes, the expression of these genes could be disrupted by the instant method, to prevent or forestall a respective type of cancer. This disruption would be via linkages to the mRNA generated from the cancer genes.

EXAMPLE 3

HER-2/neu-AA

The HER-2/neu proto-oncogene encodes a growth factor receptor that is over-expressed in 20–30% of metastatic breast cancers. This over-expression is associated with decreased survival and decreased relapse-free periods. The anti-HER2 antibody may be used as a targeting ligand for a therapeutic nanostructure as described above. Below is an amino-acid sequence for HER-2/neu-AA.

```
                                              (SEQ ID NO: 3)
MAETEERSLDNFFAKRDKKKKKERSNRAASAAGAAGSAGGSSGAAGAAGG

GAGAGTRPGDGGTASAGAAGPGAATKAVTKDEDEWKELEQKEVDYSGLRV

QAMQISSEKEEDDNEKRQDPGDNWEEGGGGGGGMEKSSGPWNKTAPVQAP

PAPVTVTETPEPAMTSGVYRPPGARLTTTRKTPQGPPE1YSDTQFPSLQS

TAKHVESRKDKEMEKSFEVVRHKNRGRDEVSKNQALKLQLDNQYAVLENQ

KSSHSQYN
```

EXAMPLE 4

Human-Erb-B

A related method for treating breast cancer utilizing nanostructures functionalized with polynucleotide ligands targets genetic mutations known to exist in tumor cells. Erb b is a protein that is unregulated in breast cancer and for which several known NA mutations exist. The method described above with reference to Examples 1 and 2 is used to deliver, to breast tumor cells, therapeutic nanostructures carrying polynucleotide ligands which are DNA strands complementary to identified mutated genetic material. Amino acids comprising the erb b protein are as follows:

```
                                              (SEQ ID NO: 4)
MELAALCRWGLLLALLPPGAASTQVCTGTDMKLRLPASPETHLDMLRHLY

QGCQVVQGNLELTYLPTNASLSFLQDIQEVQGYVLIAHNQVRQVPLQRLR

IVRGTQLFEDNYALAVLDNGDPLNNTTPVTGASPGGLRELQLRSLTEILK

GGVLIQRNIQLCYQDTILWKDITHRNNQLALTLIDTNRSRACHPCSPMCK

GSRCWGESSEDCQSLTRTVCAGGCARCKGPLPTDCCHEQCAAGCTGPKHS

DCLACLHFNIISGICELHCPALVTYNTDTFESMPNPEGRYTFGASCVTAC

PYNYLSTDVGSCTLVCPLHNQEVTAEDGTQRCEKCSKPCARVCYGLGMEH

LREVRAVTSANIQEFAGCKiKJFGSLAFLPESFDGDPASNTAPLQPEQLQ

VFETLEEITGYLYISAWPDSLPDLSVFQNLQVIRGRTLHNGAYSLTLQGL

GJSWLGLRSLRELGSGLALIHHNTHLCFVHTVPWDQLFRNPHQALLHTAN

RPEDECVGEGLACHQLCARGHCWGPGPTQCVNCSQFLRGQECVEECRVLQ

GLPREYVNARHCLPCHPECQPQNGSVTCFGPEADQCVACAHYKDPPFCVA

RCPSGVKPDLSYMPIWKFPDEEGACQPCPINCTHSCVDLDDKGCPAEQRA

SPLTSJVSAVVGILLVVVLGVVFGILIKRRQQKIRKYTMRRLLQETELVE

PLTPSGAMPNQAQMRILKETELRKVKVLGSGAFGTVYKGIWIIDGENVKJ

PVAIKVLRENTSPKANKEILDEAYVMAGVGSPYVSRLLGICLTSTVQLVT

QLMPYGCLLDHVRENRGRLGSQDLLNWCMQIAKGMSYLEDVRLVHRDLAA

RNVLVKSPNHVKITDFGLARLLDIDETEYHADGGKVPHWMALESILRRRF

THQSDVWSYGVTVWELMTFGAKPYDGIPAREIIPDLLEKGERLPQPPICT

IIDVYMIMVKCWMIDSECRPRFRELVSEFSRMARDPQRFVVIQNEDLGPA

SPLDSTFYRSLLEDDDMGDLVDAEEYLVPQQGFFCPDPAPGAGGMVHHRI

IRSSSTRSGGGDLTLGLEPSEEEAPRSPLAPSEGAGSDVFDGDLGMGAAK

GLQSLPTHDPSPLQRYSEDPTVPLPSETDGYVAPLTCSPQPEYVNQPDVR
```

-continued

PQPPSPREGPLPAARPAGATLERAKTLSPGKNGVVKDVFAFGGAVENPEY

LTPQGGAAPQPHPPPAFSPAFDNLYYWDQDPPERGAPPSTFKGTPTAENP

EYLGLDVPV

The erb b protein may serve itself as the target structure for a therapeutic nanostructure pursuant to the techniques described herein. In general, where a protein is over-expressed in tumor cells and thus serves as a tumor-cell marker, an antibody may be selected or constructed for attaching to that over-expressed protein to destroy the affected cell.

EXAMPLE 5

Treatment of Exocrine Gland Cancer

Therapeutic heating elements realized as nanotube antennas provided with appropriate targeting ligands may be used to destroy the epithelium of an exocrine gland, particularly the mammary gland, in the prophylactic and therapeutic treatment of cancer. The nanotube heating elements are coupled to cells of the ductal epithelium to induce disruption or disruption of the cells. More particularly, coupling is effectuated via targeting of cell-surface markers, receptor ligands, e.g., ligands to gastrin-releasing peptide-like receptors, tumor-associated antigens, e.g., the 57 kD cytokeratin or the antigen recognized by the monoclonal antibody GB24, the extracellular matrix glycoprotein tamascin, antisense oncogenes such as c-fos, homeobox genes that are expressed in cancer cells but not normal cells, tumor-infiltrating lymphocytes that express cytokines, RGD-containing peptides and proteins, which are administered following surgery, lipophilic drug-containing liposomes to which are covalently conjugated monoclonal antibodies for targeting to cancer cells, low fat diet, moderate physical exercise and hormonal modulation. For prostate cancer, anti-testosterone agents can be used as well as an inhibitor of cell proliferation produced by prostatic stromal cells and C-CAM, an epithelial cell adhesion molecule.

See U.S. Pat. No. 6,330,472 to Sukamar, the pertinent portions of that disclosure being incorporated by reference herein.

EXAMPLE 6

Treatment of Prostate Cancer

Nanotube antenna-heating elements provided with appropriate targeting ligands may be used to destroy tumor cells of the prostate gland. In particular, designer peptides or antibodies are used as ligands for connecting to target proteins in the form of transmembrane antigens expressed or overly expressed in tumor cells of the prostate gland. These target proteins are cell surface serpentine transmembrane antigens exclusively or predominantly expressed in the prostate, as well as in prostate cancer, and termed "STEAP" ("Six Transmembrane Epithelial Antigen of the Prostate"). The antigens are particularly described in U.S. Pat. No. 6,329,503, pertinent portions of the disclosure of which are hereby incorporated by reference. It is to be noted that the human STEAPs exhibit a high degree of structural conservation among them but show no significant structural homology to any known human proteins. A particularly effective target protein candidate is STEAP-1, a type IIIa membrane protein expressed predominantly in prostate cells in normal human tissues. Structurally, STEAP-1 is a 339 amino acid protein characterized by a molecular topology of six transmembrane domains and intracellular N- and C-termini, suggesting that it folds in a "serpentine" manner into three extracellular and two intracellular loops. STEAP-1 protein expression is maintained at high levels across various stages of prostate cancer. Moreover, STEAP-1 is highly over-expressed in certain other human cancers. In particular, cell surface expression of STEAP-1 has been definitively confirmed in a variety of prostate and prostate cancer cells, bladder cancer cells and colon cancer cells. These characteristics indicate that STEAP-1 is a specific cell-surface tumor antigen expressed at high levels in prostate, bladder, colon, and other cancers. STEAP-2, like STEAP-1, is prostate-specific in normal human tissues and is also expressed in prostate cancer.

U.S. Pat. No. 6,329,503 discloses polynucleotides corresponding or complementary to all or part of the STEAP genes, mRNAs, and/or coding sequences, preferably in isolated form, including polynucleotides encoding STEAP proteins and fragments thereof, DNA, RNA, DNA/RNA hybrid, and related molecules, polynucleotides or oligonucleotides complementary to the STEAP genes or mRNA sequences or parts thereof, and polynucleotides or oligonucleotides which hybridize to the STEAP genes, mRNAs, or to STEAP-encoding polynucleotides. In addition, the disclosure of U.S. Pat. No. 6,329,503 provides STEAP proteins and polypeptide fragments thereof. Ligands for connecting nanotubes to STEAP-1 and STEAP-2 are made pursuant to these polynucleotides, STEAP proteins and polypeptide fragments thereof. U.S. Pat. No. 6,329,503 discloses further provides antibodies that bind to STEAP proteins and polypeptide fragments thereof, including polyclonal and monoclonal antibodies, murine and other mammalian antibodies, chimeric antibodies, humanized and fully human antibodies, and antibodies labeled with a detectable marker, and antibodies conjugated to radionucleotides, toxins or other therapeutic compositions. These antibodies may serve as ligands and targeting moieties.

Further target structures for functionalized nanostructures include cancer markers and cell-surface viral antigens expressed on infected cells. Some examples include CD19, CD22, CD 20, CD 25, gp41, gp120, etc. It is to be noted that many target structures are cell lineage specific, pathogen specific, tumor cell specific, activation-specific, etc. Accordingly, the nanostructures will selectively avoid or ignore healthy cells, tissues, and organs.

Figure 4:
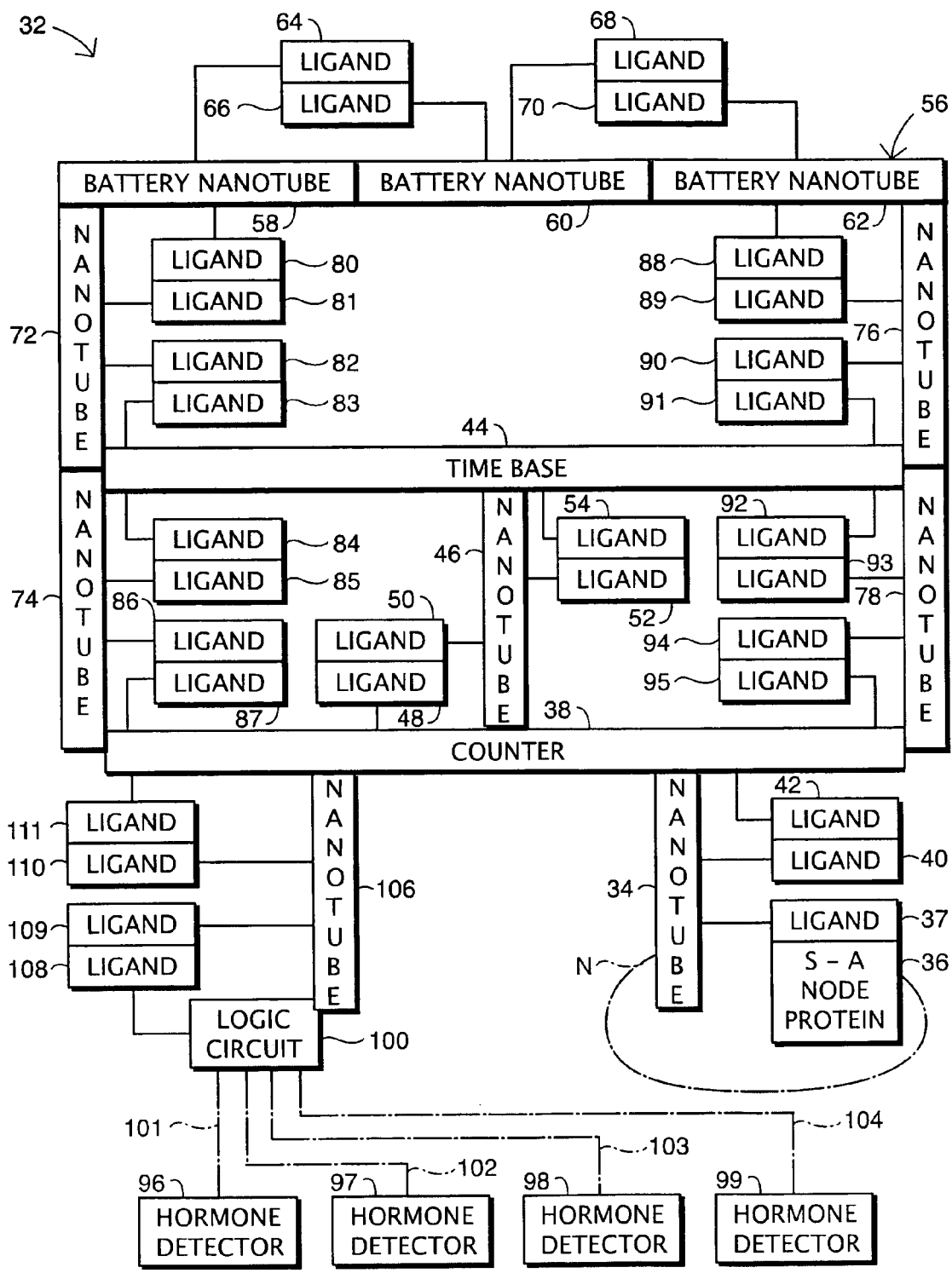
FIG. 4 is a block diagram of a pacemaker assembled inside a patient from self-coupling nanostructures, pursuant to a method of the present invention.

FIG. 4 schematically illustrates a nanocircuit 32 assembled on site inside a patient (not separately shown) for performing a pacemaker function. Nanocircuit 32 comprises a plurality of different nanostructures which self-couple to one another by virtue of their ligands. In a conceptually most simple deployment procedure, the different nanostructures of nanocircuit 32 are injected in the patient in seriatim to control the sequence of interconnection and accordingly the form of nanocircuit 32. In an alternative delivery technique, the various components of nanocircuit 32 are provided with downstream ligands which are temporarily locked, masked, or deactivated and which become active only when an upstream ligand is activated by connection of its respective nanostructure to one or more respective upstream nanostructures.

As illustrated in FIG. 4, a nanotube 34 is connected at one end to a preselected protein 36 of an S-A node N of a patient's heart via a ligand 37 carried by the nanotube.

Nanotube 34 is thus electrically inserted at that one end in the S-A node N. At an opposite end, nanotube 34 is operatively connected to an output (not designated) of a counter nanostructure 38. That conductive or electrical connection between nanotube 34 and counter 38 is enabled by a molecular coupling of ligands 40 and 42 carried by nanotube 34 and counter 38, respectively. Ligands 40 and 42 may be both nucleotide sequences (complementary strands uniquely fitted to one another), or antigen and antibody pairs. Ligands 40 and 42 are keyed to attach only to each other and not to any other structure in the patient.

A counting input (not designated) of counter 38 is operatively tied to a clock output (not designated) of a time base nanostructure 44 via a nanotube 46. This electrical connection is realized by a first pair of ligands 48 and 50 and a second pair of ligands 52 and 54. Ligands 48 and 50 are pre-attached to counter 38 and nanotube 46, respectively. At the site of the S-A node, ligands 48 and 50 couple to one another. Likewise ligands 52 and 54 are respectively carried on nanotube 46 and time base 44 and couple to one another at the S-A node of the patient.

Nanotube 46 is passivated except at its ends, for instance, by an insulating sheath such as a layer of silicon nitride or silicon oxide. This sheath is permanent, i.e., endures as long as the effective life of nanotube 46. All other nanostructures of nanocircuit 32 are similarly passivated to provide appropriate insulation from electrolytes in the patient. At locations where a connection is to be made to another nanotube or nanostructure, the nanotubes may be temporarily passivated, for instance, with a cap or cover made of a suitable insulating bioabsorbable polymer. Such polymers are well known in the medical industry. The bioabsorbable cap or cover functions to electrically insulate and protect the active points during storage and transport. Once a target site is attained, the polymer degrades or disintegrates to permit the self-assembly and activation processes.

It is to be noted that the nanostructures of FIG. 4, as well as all nanostructures utilizable in situ as described herein may be provided with a passivation layer which accomplishes the additional function of protecting or insulating the nanostructures from chemical and biochemical action of various natural constituents of body fluids, such as calcium and phosphate ions. These ions might tend to precipitate and agglomerate onto the nanostructures. In addition, the natural clotting action of the blood might interfere with the intended operation of the nanostructures. To obviate these eventualities, implantable nanostructures are provided with a layer or coating, which may serve a dual purpose of electrical insulation and biochemical isolation. Alternatively, more than one passivation layer may be provided, for instance, a first layer of silicon nitride or silicon oxide for purposes of electrical insulation and a second layer of an oil, a protein sheath or a viral shell may be formed over the nanostructure. The oil may be in the form of a liposome, while the protein sheath may be a blood protein such as alpha globulin. An example of a viral shell is that of an anodenal virus.

Counter 38 and time base 44 are powered by a supply 56 comprising a plurality of nanotube batteries 58, 60, 62 operatively connected to each other, for instance, in series by respective pairs of ligands 64, 66 and 68, 70. These ligands are attached in the manufacturing process to respective battery nanotubes 58, 60, 62 and selectively couple to one another in situ to form power supply 56. Nanotube batteries 58, 60, 62 are each provided at opposite ends with elements of different valences or electron affinities, such as copper (or carbon) and zinc (not shown). It is to be observed that wherever a ground or return circuit is required, the body fluids of the patient may function to provide that functionality.

Power supply 56 is operatively linked via conductive nanotubes 72, 74, 76, 78 to power inputs or contacts (not designated) of counter 38 and time base 44. Mechanical, as opposed to electrical, connection is provided by pairs of ligands 80, 81 and 82, 83, and 84, 85, and 86, 87, and 88, 89, and 90, 91 and 92, 93, and 94, 95.

Nanocircuit 32 generates, at the counting output of counter 38, a periodic pulse which is applied via nanotube 34 to S-A node N of the patient's heart, thereby stimulating a myocardial contraction. The rate at which pulses are generated may be automatically varied by including in nanocircuit 32 a plurality of hormone detectors 96, 97, 98, 99 which are realized as nanostructures. Hormone detectors 96–99 include receptor sites for temporary binding to cardiac-specific hormones and are thus keyed to generate a signal in the presence of the hormones. Detectors 96–99 are linked to a logic nanostructure 100 by respective ligands and nanotubes schematically and collectively indicated at 101–104. Logic nanostructure or circuit 100 is in turn connected to a maximum-count-setting input (not designated) of counter 38 via a nanotube wire or filament 106 and ligands 108–111. Depending on the hormone concentration, counter 38 provides a pulse output of greater or lesser frequency.

Further digital or analog control may be provided for nanocircuit 32. It is to be noted that this additional control, and any nanocircuitry used in the present methodology, may be partially preassembled, during manufacture, and realized by fixed or hardware circuitry contained within the various nanostructures. Alternatively, control circuits may be assembled and programmed in situ in the patient via chemical, magnetic, electromagnetic, proton, acoustic or other remote means of manipulation to change rate and function in response to an internal electrochemical state such as the production of heart attack protein.

Figure 5:
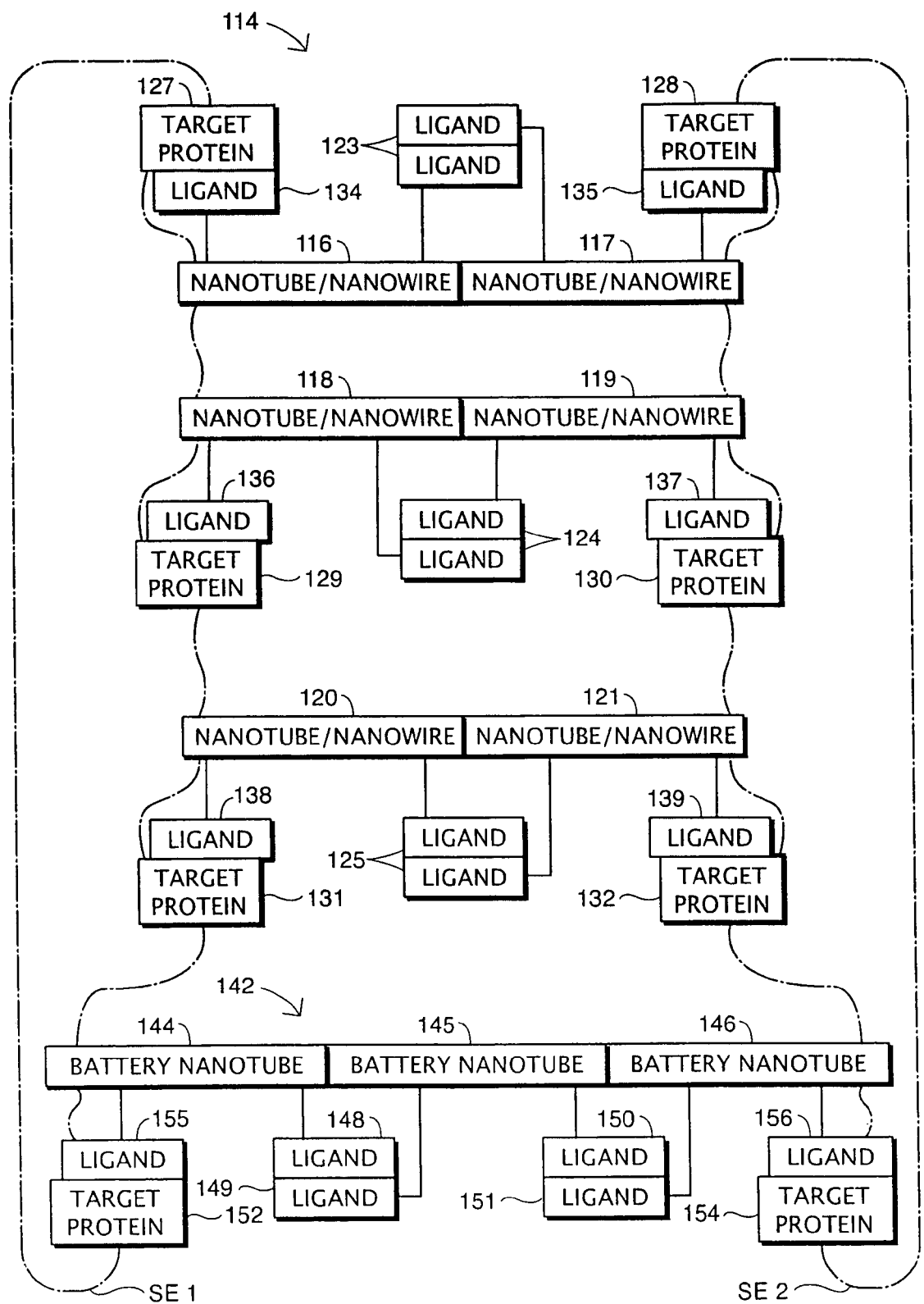
FIG. 5 is a block diagram showing a nanocircuit connecting severed portions of a nerve fiber, the nanocircuit being self-assembled on location pursuant to the present invention.

FIG. 5 depicts a nanocircuit 114 comprising a plurality of nanostructures assembled in situ to each other and to severed ends SE1 and SE2 of a nerve fiber (not separately designated). More specifically, nanocircuit 114 includes a plurality of nanowires or nanotubes 116, 117 and 118, 119, and 120, 121 connected in pairs to one another via ligands 123, 124, 125 and to target proteins or other molecules 127, 128 and 129, 130 and 131, 132 in severed ends SE1 and SE2 via ligands 134–139. Nanotube pairs 116, 117 and 118, 119, and 120, 121 form respective parallel-connected circuit paths between ends SE1 and SE2 for carrying therebetween current generated by a power source 142. Power source 142 comprises a plurality of nanotube battery cells 144, 145, 146 assembled in situ to each other to form a series (or, alternatively, parallel) circuit component. The battery cells 144–146 are operatively connected to each other via keyed pairs of ligands 148, 149 and 150, 151 and to target proteins or other molecules 152 and 154 via ligands 155 and 156.

Upon the assembly of nanocircuit 114 inside a patient's nervous system, current flows between severed nerve ends SE 1 and SE2 over nanotube/nanowire pairs 116, 117 and 118, 119, and 120, 121 under the action of power source 142. This electrical current assists in the repair of nerve ends SE1 and SE2, i.e., in a reattachment of the nerve ends to one another. It is to be understood that in an actual application, the circuit of FIG. 5 comprises millions or even billions of nanostructures connected end-to-end to form a single wire or meshes of interconnected conducting strands connecting severed ends SE1 and SE2 to one another.

It can be appreciated from the specific embodiments of medical nanotechnology described above that nanostructures may be used in the treatment of many kinds of injuries and diseases, whether of an infectious nature, a genetic nature, systemic, or localized. Where the nanostructure devices are to operate as antibiotics (FIGS. 1–3), target molecules serving as attachment sites may be located in or on the cell membranes as described above with reference to FIG. 3. Alternatively, ligands may be provided which enable a transport of the nanostructures 12 inside target cells. The ligands may in that case attach to transport mechanisms in a cell membrane. Alternatively, nanostructures such as nanotube heating elements 12 may be coated with a protein sheath enabling passage into selected kinds of cells.

Other kinds of disease states treatable by the present methodology include gout where urea crystal deposits in extremities may be reversed. It is contemplated that nanobatteries, i.e., nanotubes provided at opposite ends with elements having different electron affinities, are attached via respective ligands to the urea crystals. In the body fluids, the batteries conduct current and break down the urea deposits in a basic chemical reaction. As mentioned above, the nanotubes may be temporarily passivated at their ends with bioabsorbable polymers to prevent conduction until the nanotubes have had sufficient opportunity to latch onto a urea deposit.

Where the target cells are fat cells (receptors: toll cells), use of the present methodology may lead to permanent weight reduction. Where the target cells are nerve cells, and particularly, the axons in the peripheral nervous system, the present methodology may be used to sever nerve fibers and thus reduce pain.

The present invention is also useful in the acquisition of information for the performance of medical diagnoses such as monitoring the state of the endocrine system, reporting on the glucose level in the blood, measuring the heart rate, etc. Detection may be achieved by molecular probes connected in significant groups to a transmitter assembled inside the body. Many diagnostic functions are accomplished inductively, with measurement outside the body of accumulated activated nanostructures.

Nanobatteries as discussed herein may be encapsulated with electrolyte and passivated or provided with a semipermeable one-way membrane to use the body fluid as an electrolyte for battery function.

It is contemplated that for purposes of most diagnostic and therapeutic procedures involving the delivery of carbon nanostructures to a human being or other lifeform, the carbon nanostructures are provided with covalently bonded ligands that determine the target sites to which the nanostructures will bind. Covalent bonding to a host of different protein polypeptide ligands may be effectuated by oxidizing the carbon nanostructures to form carboxyl or carbonyl groups that are then reacted with amine groups on the protein polypeptide ligands to form covalent linkages. The covalent bonding may occur at the ends of carbon nanotubes or internally at breaks in the regular carbon lattice.

More specifically, covalent bonding to a host of different protein polypeptide ligands may be effectuated by oxidizing the carbon nanostructures to form hydroxyl groups that are then (a) esterified with the carboxylic acid or carboxyl group of a protein to form a COO-peptide link or (b) aminated to provide an amine group on the nanostructure (CNT), which is then reacted with isocyanate or isothiocyanate to form a structure CNT-N=C=O or CNT-N=C=S, which is then reacted with an amine group on a polypeptide to connect the polypeptide to the CNT via a urethane group:

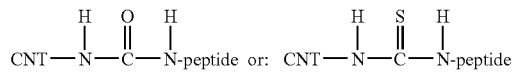

Alternatively, ligands may be bound non-specifically to the carbon nanostructures. It has been found, for instance, that the protein amelogenin may be nonspecifically bound to carbon nanotubes. Pursuant to the methodology for non-specific binding, carbon nanotubes are activated by heating in boiling water (e.g., for 10 minutes). The boiling serves to provide free COOH groups for coupling of protein to the carbon nanotubes. The activated nanotubes are mixed with a selected ligand protein and optionally with a cross-linker such as EDC (1-(ethyl-3-[3-dimethylaminopropyl]carbodiimide hydrochloride) (e.g., for two hours). The resultant non-specifically functionalized carbon nanotubes are then recovered by centrifugation onto a physical membrane.

Non-specific binding to carbon nanostructures may be the result of van der Walls forces or weak ionic forces. In general, nonspecific binding will be possible at least where a polypeptide ligand, for instance, a monoclonal antibody, is hydrophobic. Certain other, non-hydrophobic polypeptides may also be induced to nonspecifically bind to carbon nanostructures.

Where one or more predetermined types of ligand are specifically bound to a carbon nanostructure, for instance, via carboxyl groups on the nanostructure, it may be desirable to subsequently non-specifically bind an auxiliary molecule to the nanostructure for purposes of masking or blocking any unbound coupling sites such as carboxyl groups on the nanostructure. Preferably, such a masking molecule is so common in the human (or animal) body that the masking molecule itself can perform no targeting function. One or more albumins may be selected as masking agents.

It is to be noted that it is not necessary for a functionalized nanostructure to couple to its target molecule(s) in order for the present methodology to be effective. For instance, where the goal is to destroy a target cell or virus by radiation-induced heating, it is only necessary that the ligand temporarily hold the nanostructure in proximity to the target for a sufficient time to enable heating to occur. The heated nanostructure will destroy the target so long as the nanostructure is in proximity to the target.

Carbon nanostructures targeted to specific sites via appropriate ligands may be used as contrast agents in medical imaging procedures. The nanostructures provide, to the targeted tissue structures, a "coating" sufficient to enhance optical detectability in images generated by MRI or CATscan machines.

Although the invention has been described in terms of particular embodiments and applications, one of ordinary skill in the art, in light of this teaching, can generate additional embodiments and modifications without departing from the spirit of or exceeding the scope of the claimed invention. A functionalized nanostructure (one provided with an appropriate ligand) may be delivered to a target site by known methods in addition to or instead of the methods detailed hereinabove. Nanostructures may be injected into the vascular system of the patient for delivery to a target site, or injected directly into a region about the target site. The nanostructures are dispersed in a pharmaceutically suitable carrier. Alternatively or additionally, the functionalized nanostructures are disposed in liposomes. Where nanostructure treatment devices are attached to a virus carrier, the virus is also carried in a liposome. The liposomes may in turn be provided with ligands for attachment to a predetermined target structure. After this ligand-mediated attachment, the liposomes release their payload nanostructures, for instance, into a target cell.

Accordingly, it is to be understood that the drawings and descriptions herein are proffered by way of example to facilitate comprehension of the invention and should not be construed to limit the scope thereof.

What is claimed is:

1. A medical method comprising:
providing an implantable microscopic medical device including a nanostructure provided with a ligand;
inserting said medical device into a patient;
effectively attaching said nanostructure via said ligand to an instance of a predetermined type of target structure inside the patient; and
after the attaching of said nanostructure to said instance of said target structure, utilizing said nanostructure to perform a preselected medical diagnostic or therapeutic function, the utilizing of said nanostructure includes activating said nanostructure,
said nanostructure being provided with at least one additional ligand, the activating of said nanostructure including coupling said nanostructure via said additional ligand to another nanostructure deployed in the patient.

2. The method defined in claim 1 wherein the two coupled nanostructures form an electrical device, the activating of said nanostructure further including operating said electrical device.

3. The method defined in claim 2 wherein said electrical device includes a timing circuit, the activating of said nanostructure including generating an electrical event periodically under the action of said timing circuit.

4. The method defined in claim 3 wherein the attaching of said nanostructure includes anchoring said nanostructure to a predetermined site in cardiac tissue, said diagnostic or therapeutic function being a pacemaker function.

5. The method defined in claim 2 wherein the attaching of said nanostructure includes anchoring said nanostructure proximately to an injury site in a nerve, said diagnostic or therapeutic function being the generation of electrical current in injured nerve tissue to facilitate an effective repair of the injured nerve tissue.

6. The method defined in claim 5 wherein the operating of said electrical device includes inductively generating said electrical current.

7. A medical method comprising:
providing an implantable microscopic medical device including a nanostructure provided with a ligand;
inserting said medical device into a patient;
effectively attaching said nanostructure via said ligand to an instance of a predetermined type of target structure inside the patient; and
after the attaching of said nanostructure to said instance of said target structure, utilizing said nanostructure to perform a preselected medical diagnostic or therapeutic function, the utilizing of said nanostructure includes activating said nanostructure,
said medical device including a battery, the activating of said nanostructure including using a body fluid to enable ion migration under a potential generated by said battery.

8. The method defined in claim 7 wherein said target structure includes a urea deposit, the generating of ion migration serving to disrupt said urea deposit.

9. A medical method comprising:
providing an implantable microscopic medical device including a nanostructure provided with a ligand;
inserting said medical device into a patient;
effectively attaching said nanostructure via said ligand to an instance of a predetermined type of target structure inside the patient; and
after the attaching of said nanostructure to said instance of said target structure, utilizing said nanostructure to perform a preselected medical diagnostic or therapeutic function,
said ligand including an antibody or polypeptide, said predetermined type of target structure including a structure taken from the group consisting of a protein and a sequence of amino acids,
said protein being in a membrane or wall of a particular kind of cell, the utilizing of said nanostructure including fragmenting said protein and rupturing said membrane or wall.

10. The method defined in claim 9 wherein the utilizing of said nanostructure includes heating said nanostructure, said diagnostic or therapeutic function including destroying said cell.

11. A medical method comprising;
providing an implantable microscopic medical device including a nanostructure provided with a ligand;
inserting said medical device into a patient;
effectively attaching said nanostructure via said ligand to an instance of a predetermined type of target structure inside the patient; and
after the attaching of said nanostructure to said instance of said target structure, utilizing said nanostructure to perform a preselected medical diagnostic or therapeutic function,
said ligand including a DNA sequence or polynucleotide, said predetermined type of target structure including a strand of viral DNA.

12. The method defined in claim 11 wherein the utilizing of said nanostructure includes heating said nanostructure, said diagnostic or therapeutic function including destroying a microorganism containing said strand of viral DNA.

13. A medical method comprising;
providing an implantable microscopic medical device including a nanostructure provided with a ligand;
inserting said medical device into a patient;
effectively attaching said nanostructure via said ligand to an instance of a predetermined type of target structure inside the patient; and
after the attaching of said nanostructure to said instance of said target structure, utilizing said nanostructure to perform a preselected medical diagnostic or therapeutic function,
said ligand including a sequence of amino acids or polypeptide, said predetermined type of target structure including a prion.

14. A medical method comprising:
providing an implantable microscopic medical device including a nanostructure provided with a ligand;
inserting said medical device into a patient;
effectively attaching said nanostructure via said ligand to an instance of a predetermined type of target structure inside the patient; and
after the attaching of said nanostructure to said instance of said target structure, utilizing said nanostructure to perform a preselected medical diagnostic or therapeutic function,
the utilizing of said nanostructure including heating said nanostructure, thereby delivering heat energy to said instance of said target structure.

15. The method defined in claim 14 wherein the heating of said nanostructure includes inducing a current in said nanostructure.

16. The method defined in claim 15 wherein the inducing of said current includes generating, outside of the patient, an energy field and subjecting said nanostructure inside the patient to said energy field.

17. The method defined in claim 16 wherein the generating of said energy field includes transmitting into the patient wave energy of a predetermined wavelength capable of penetrating deeply into the patient.

18. The method defined in claim 17 wherein the utilizing of said nanostructure includes changing a physical shape of said nanostructure by virtue of the attaching of said nanostructure via said ligand to said instance of said predetermined type of target structure, whereby the inducing of said current by said energy field is enabled.

19. The method defined in claim 14 wherein the heating of said nanostructure includes generating a current in a circuit including said nanostructure and body fluids of the patient.

20. The method defined in claim 14 wherein the utilizing of said nanostructure includes delivering sufficient heat energy to said instance of said target structure to destroy said instance of said target structure.

21. A medical method comprising;
providing an implantable microscopic medical device including a nanostructure provided with a ligand;
inserting said medical device into a patient;
effectively attaching said nanostructure via said ligand to an instance of a predetermined type of target structure inside the patient; and
after the attaching of said nanostructure to said instance of said target structure, utilizing said nanostructure to perform a preselected medical diagnostic or therapeutic function,
said nanostructure being provided with a masking agent for blocking coupling sites on said nanostructure that are free of said ligand.

22. The method defined in claim 21 wherein the masking agent includes albumin.

23. A medical method comprising:
providing an implantable microscopic medical device including a nanostructure provided with a ligand;
inserting said medical device into a patient;
effectively attaching said nanostructure via said ligand to an instance of a predetermined type of target structure inside the patient; and
after the attaching of said nanostructure to said instance of said target structure, utilizing said nanostructure to perform a preselected medical diagnostic or therapeutic function,
said nanostructure having opposing ends provided with components of different valences, the activating of said nanostructure including using a body fluid to enable ion migration under a potential generated between said components.

24. A medical method comprising:
providing an implantable microscopic medical device including a nanostructure provided with a ligand;

inserting said medical device into a patient;

effectively attaching said nanostructure via said ligand to an instance of a predetermined type of target structure inside the patient; and after the attaching of said nanostructure to said instance of said target structure, utilizing said nanostructure to perform a preselected medical diagnostic or therapeutic function, said nanostructure being passivated.

25. A medical method comprising:

providing an implantable microscopic medical device including a nanostructure provided with a ligand;

inserting said medical device into a patient;

effectively attaching said nanostructure via said ligand to an instance of a predetermined type of target structure inside the patient;

after the attaching of said nanostructure to said instance of said target structure, utilizing said nanostructure to perform a preselected medical diagnostic or therapeutic function; and inserting said nanostructure into a cell, the activating of said nanostructure including heating said nanostructure and destroying said cell.

26. A medical method comprising:

providing an implantable microscopic medical device including a nanostructure provided with a ligand;

inserting said medical device into a patient;

effectively attaching said nanostructure via said ligand to an instance of a predetermined type of target structure inside the patient; and after the attaching of said nanostructure to said instance of said target structure, utilizing said nanostructure to perform a preselected medical diagnostic or therapeutic function, the utilizing of said nanostructure including destroying said target structure, the utilizing of said nanostructure further including fragmenting or rupturing said target structure.

* * * * *

SEQUENCE LISTING

<160> NUMBER OF SEQ ID NOS: 4

<210> SEQ ID NO 1
<211> LENGTH: 552
<212> TYPE: DNA
<213> ORGANISM: Hepatitis B virus

<400> SEQUENCE: 1

```
atggacattg acccgtataa agaatttgga gcttctgtgg agttactctc ttttttgcct     60
tctgacttct ttccttctat tcgagatctc ctcgacaccg cctcagctct gtatcggag    120 gccttagagt ctccggaaca ttgttctcct caccatacag cactaaggca agagattctg    180
tgttggggtg agttgatgaa tctggccacc tgggtgggaa gtaatttgga agacccagca    240
tccagggaat tagtagtcag ctatgtcaat gttaatatgg gcctgaaaat cagacaacta    300
ctgtggtttc acatttcctg tcttactttt ggaagagaaa ctgtacttga gtatttggtg    360
tcttttggag tgtggattcg cactcctctt gcttatagac caccaaatgc ccctatctta    420
tcaacacttc cggaaactac tgttgttaga cgacgaggca ggtcccctag aagaagaact    480
ccctcgcctc gcagacgaag gtctcaatcg ccgcgtcgca gaagatctca atctcgggaa    540
cctcaatgtt ag                                                       552
```

<210> SEQ ID NO 2
<211> LENGTH: 291
<212> TYPE: DNA
<213> ORGANISM: Human immunodeficiency virus

<400> SEQUENCE: 2

```
atggaacaag ccccagaaga ccaggggcca cagagggagc catacaatga atggacacta     60
gagcttttag aggagcttaa gaatgaagct gttagacatt ttcctaggcc atggctccac    120
agcttaggac aacatatcta taacacctat ggggatactt gggagggagt tgaagctata    180
ataaggatat tgcaacaact actgtttatc catttcagaa ttgggtgcca tcatagcaga    240
ataggcatta ttcgacagag aagagtaaga aatggagcta gtagatccta a            291
```

<210> SEQ ID NO 3
<211> LENGTH: 258
<212> TYPE: PRT
<213> ORGANISM: Homo sapiens

<400> SEQUENCE: 3

```
Met Ala Glu Thr Glu Glu Arg Ser Leu Asp Asn Phe Phe Ala Lys Arg
  1               5                  10                  15

Asp Lys Lys Lys Lys Glu Arg Ser Asn Arg Ala Ala Ser Ala Ala
             20                  25                  30

Gly Ala Ala Gly Ser Ala Gly Gly Ser Ser Gly Ala Ala Gly Ala Ala
         35                  40                  45

Gly Gly Gly Ala Gly Ala Gly Thr Arg Pro Gly Asp Gly Thr Ala
     50                  55                  60

Ser Ala Gly Ala Ala Gly Pro Gly Ala Ala Thr Lys Ala Val Thr Lys
 65                  70                  75                  80
```

-continued

```
Asp Glu Asp Glu Trp Lys Glu Leu Glu Gln Lys Glu Val Asp Tyr Ser
                85                  90                  95
Gly Leu Arg Val Gln Ala Met Gln Ile Ser Ser Glu Lys Glu Glu Asp
            100                 105                 110
Asp Asn Glu Lys Arg Gln Asp Pro Gly Asp Asn Trp Glu Glu Gly Gly
        115                 120                 125
Gly Gly Gly Gly Gly Met Glu Lys Ser Ser Gly Pro Trp Asn Lys Thr
    130                 135                 140
Ala Pro Val Gln Ala Pro Pro Ala Pro Val Ile Val Thr Glu Thr Pro
145                 150                 155                 160
Glu Pro Ala Met Thr Ser Gly Val Tyr Arg Pro Pro Gly Ala Arg Leu
                165                 170                 175
Thr Thr Thr Arg Lys Thr Pro Gln Gly Pro Pro Glu Ile Tyr Ser Asp
            180                 185                 190
Thr Gln Phe Pro Ser Leu Gln Ser Thr Ala Lys His Val Glu Ser Arg
        195                 200                 205
Lys Asp Lys Glu Met Glu Lys Ser Phe Glu Val Val Arg His Lys Asn
    210                 215                 220
Arg Gly Arg Asp Glu Val Ser Lys Asn Gln Ala Leu Lys Leu Gln Leu
225                 230                 235                 240
Asp Asn Gln Tyr Ala Val Leu Glu Asn Gln Lys Ser Ser His Ser Gln
                245                 250                 255
Tyr Asn

<210> SEQ ID NO 4
<211> LENGTH: 1255
<212> TYPE: PRT
<213> ORGANISM: Homo sapiens

<400> SEQUENCE: 4

Met Glu Leu Ala Ala Leu Cys Arg Trp Gly Leu Leu Ala Leu Leu
  1               5                  10                  15
Pro Pro Gly Ala Ala Ser Thr Gln Val Cys Thr Gly Thr Asp Met Lys
                20                  25                  30
Leu Arg Leu Pro Ala Ser Pro Glu Thr His Leu Asp Met Leu Arg His
            35                  40                  45
Leu Tyr Gln Gly Cys Gln Val Val Gln Gly Asn Leu Glu Leu Thr Tyr
        50                  55                  60
Leu Pro Thr Asn Ala Ser Leu Ser Phe Leu Gln Asp Ile Gln Glu Val
65                  70                  75                  80
Gln Gly Tyr Val Leu Ile Ala His Asn Gln Val Arg Gln Val Pro Leu
                85                  90                  95
Gln Arg Leu Arg Ile Val Arg Gly Thr Gln Leu Phe Glu Asp Asn Tyr
            100                 105                 110
Ala Leu Ala Val Leu Asp Asn Gly Asp Pro Leu Asn Asn Thr Thr Pro
        115                 120                 125
Val Thr Gly Ala Ser Pro Gly Gly Leu Arg Glu Leu Gln Leu Arg Ser
    130                 135                 140
Leu Thr Glu Ile Leu Lys Gly Gly Val Leu Ile Gln Arg Asn Pro Gln
145                 150                 155                 160
Leu Cys Tyr Gln Asp Thr Ile Leu Trp Lys Asp Ile Phe His Lys Asn
                165                 170                 175
Asn Gln Leu Ala Leu Thr Leu Ile Asp Thr Asn Arg Ser Arg Ala Cys
            180                 185                 190
```

-continued

```
His Pro Cys Ser Pro Met Cys Lys Gly Ser Arg Cys Trp Gly Glu Ser
            195                 200                 205

Ser Glu Asp Cys Gln Ser Leu Thr Arg Thr Val Cys Ala Gly Gly Cys
    210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
            245                 250                 255

His Phe Asn His Ser Gly Ile Cys Glu Leu His Cys Pro Ala Leu Val
            260                 265                 270

Thr Tyr Asn Thr Asp Thr Phe Glu Ser Met Pro Asn Pro Glu Gly Arg
            275                 280                 285

Tyr Thr Phe Gly Ala Ser Cys Val Thr Ala Cys Pro Tyr Asn Tyr Leu
            290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
            325                 330                 335

Pro Cys Ala Arg Val Cys Tyr Gly Leu Gly Met Glu His Leu Arg Glu
            340                 345                 350

Val Arg Ala Val Thr Ser Ala Asn Ile Gln Glu Phe Ala Gly Cys Lys
            355                 360                 365

Lys Ile Phe Gly Ser Leu Ala Phe Leu Pro Glu Ser Phe Asp Gly Asp
            370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
            405                 410                 415

Asp Ser Leu Pro Asp Leu Ser Val Phe Gln Asn Leu Gln Val Ile Arg
            420                 425                 430

Gly Arg Ile Leu His Asn Gly Ala Tyr Ser Leu Thr Leu Gln Gly Leu
            435                 440                 445

Gly Ile Ser Trp Leu Gly Leu Arg Ser Leu Arg Glu Leu Gly Ser Gly
            450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
            485                 490                 495

Ala Asn Arg Pro Glu Asp Glu Cys Val Gly Glu Gly Leu Ala Cys His
            500                 505                 510

Gln Leu Cys Ala Arg Gly His Cys Trp Gly Pro Gly Pro Thr Gln Cys
            515                 520                 525

Val Asn Cys Ser Gln Phe Leu Arg Gly Gln Glu Cys Val Glu Glu Cys
530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
            565                 570                 575

Phe Gly Pro Glu Ala Asp Gln Cys Val Ala Cys Ala His Tyr Lys Asp
            580                 585                 590

Pro Pro Phe Cys Val Ala Arg Cys Pro Ser Gly Val Lys Pro Asp Leu
            595                 600                 605

Ser Tyr Met Pro Ile Trp Lys Phe Pro Asp Glu Glu Gly Ala Cys Gln
```

-continued

```
            610                 615                 620
Pro Cys Pro Ile Asn Cys Thr His Ser Cys Val Asp Leu Asp Asp Lys
625                 630                 635                 640

Gly Cys Pro Ala Glu Gln Arg Ala Ser Pro Leu Thr Ser Ile Val Ser
            645                 650                 655

Ala Val Gly Ile Leu Leu Val Val Leu Gly Val Val Phe Gly
            660                 665                 670

Ile Leu Ile Lys Arg Arg Gln Gln Lys Ile Arg Lys Tyr Thr Met Arg
            675                 680                 685

Arg Leu Leu Gln Glu Thr Glu Leu Val Glu Pro Leu Thr Pro Ser Gly
690                 695                 700

Ala Met Pro Asn Gln Ala Gln Met Arg Ile Leu Lys Glu Thr Glu Leu
705                 710                 715                 720

Arg Lys Val Lys Val Leu Gly Ser Gly Ala Phe Gly Thr Val Tyr Lys
            725                 730                 735

Gly Ile Trp Ile Pro Asp Gly Glu Asn Val Lys Ile Pro Val Ala Ile
            740                 745                 750

Lys Val Leu Arg Glu Asn Thr Ser Pro Lys Ala Asn Lys Glu Ile Leu
            755                 760                 765

Asp Glu Ala Tyr Val Met Ala Gly Val Gly Ser Pro Tyr Val Ser Arg
770                 775                 780

Leu Leu Gly Ile Cys Leu Thr Ser Thr Val Gln Leu Val Thr Gln Leu
785                 790                 795                 800

Met Pro Tyr Gly Cys Leu Leu Asp His Val Arg Glu Asn Arg Gly Arg
            805                 810                 815

Leu Gly Ser Gln Asp Leu Leu Asn Trp Cys Met Gln Ile Ala Lys Gly
            820                 825                 830

Met Ser Tyr Leu Glu Asp Val Arg Leu Val His Arg Asp Leu Ala Ala
            835                 840                 845

Arg Asn Val Leu Val Lys Ser Pro Asn His Val Lys Ile Thr Asp Phe
            850                 855                 860

Gly Leu Ala Arg Leu Leu Asp Ile Asp Glu Thr Glu Tyr His Ala Asp
865                 870                 875                 880

Gly Gly Lys Val Pro Ile Lys Trp Met Ala Leu Glu Ser Ile Leu Arg
            885                 890                 895

Arg Arg Phe Thr His Gln Ser Asp Val Trp Ser Tyr Gly Val Thr Val
            900                 905                 910

Trp Glu Leu Met Thr Phe Gly Ala Lys Pro Tyr Asp Gly Ile Pro Ala
            915                 920                 925

Arg Glu Ile Pro Asp Leu Leu Glu Lys Gly Glu Arg Leu Pro Gln Pro
930                 935                 940

Pro Ile Cys Thr Ile Asp Val Tyr Met Ile Met Val Lys Cys Trp Met
945                 950                 955                 960

Ile Asp Ser Glu Cys Arg Pro Arg Phe Arg Glu Leu Val Ser Glu Phe
            965                 970                 975

Ser Arg Met Ala Arg Asp Pro Gln Arg Phe Val Val Ile Gln Asn Glu
            980                 985                 990

Asp Leu Gly Pro Ala Ser Pro Leu Asp Ser Thr Phe Tyr Arg Ser Leu
            995                 1000                1005

Leu Glu Asp Asp Asp Met Gly Asp Leu Val Asp Ala Glu Glu Tyr Leu
            1010                1015                1020

Val Pro Gln Gln Gly Phe Phe Cys Pro Asp Pro Ala Pro Gly Ala Gly
1025                1030                1035                1040
```

-continued

```
Gly Met Val His His Arg His Arg Ser Ser Ser Thr Arg Ser Gly Gly
                1045                1050                1055

Gly Asp Leu Thr Leu Gly Leu Glu Pro Ser Glu Glu Glu Ala Pro Arg
                1060                1065                1070

Ser Pro Leu Ala Pro Ser Glu Gly Ala Gly Ser Asp Val Phe Asp Gly
        1075                1080                1085

Asp Leu Gly Met Gly Ala Ala Lys Gly Leu Gln Ser Leu Pro Thr His
    1090                1095                1100

Asp Pro Ser Pro Leu Gln Arg Tyr Ser Glu Asp Pro Thr Val Pro Leu
1105                1110                1115                1120

Pro Ser Glu Thr Asp Gly Tyr Val Ala Pro Leu Thr Cys Ser Pro Gln
                1125                1130                1135

Pro Glu Tyr Val Asn Gln Pro Asp Val Arg Pro Gln Pro Pro Ser Pro
                1140                1145                1150

Arg Glu Gly Pro Leu Pro Ala Ala Arg Pro Ala Gly Ala Thr Leu Glu
                1155                1160                1165

Arg Ala Lys Thr Leu Ser Pro Gly Lys Asn Gly Val Val Lys Asp Val
    1170                1175                1180

Phe Ala Phe Gly Gly Ala Val Glu Asn Pro Glu Tyr Leu Thr Pro Gln
1185                1190                1195                1200

Gly Gly Ala Ala Pro Gln Pro His Pro Pro Pro Ala Phe Ser Pro Ala
                1205                1210                1215

Phe Asp Asn Leu Tyr Tyr Trp Asp Gln Asp Pro Pro Glu Arg Gly Ala
                1220                1225                1230

Pro Pro Ser Thr Phe Lys Gly Thr Pro Thr Ala Glu Asn Pro Glu Tyr
        1235                1240                1245

Leu Gly Leu Asp Val Pro Val
    1250                1255
```